(12) United States Patent
Masi et al.

(10) Patent No.: US 6,184,316 B1
(45) Date of Patent: Feb. 6, 2001

(54) CATALYST AND PROCESS FOR THE SYNDIOTACTIC POLYMERIZATION OF VINYLAROMATIC COMPOUNDS

(75) Inventors: Francesco Masi, Sant'angelo Lodigiano; Riccardo PO', Livorno; Francesco Menconi, Massa Macinaia-Lucca; Giuseppe Conti, Frosinone; Francesco Ciardelli; Angelina Altomare, both of Pisa; Federico Orsini, Livorno; Roberto Santi; Nicoletta Cardi, both of Novara, all of (IT)

(73) Assignee: Enichem S.p.A., Milan (IT)

( * ) Notice: Under 35 U.S.C. 154(b), the term of this patent shall be extended for 0 days.

(21) Appl. No.: 09/030,162

(22) Filed: Feb. 25, 1998

(30) Foreign Application Priority Data

Feb. 27, 1997 (IT) ................................. MI97A0432
Feb. 27, 1997 (IT) ................................. MI97A0431

(51) Int. Cl.⁷ ............................. C08F 12/06; C08F 4/649
(52) U.S. Cl. .................. 526/142; 526/127; 526/128; 526/140; 526/141; 526/143; 526/150; 526/151; 526/160; 526/347.2; 502/121; 502/122; 502/124; 502/125; 502/129; 502/131; 502/154
(58) Field of Search .................... 502/125, 127, 502/154, 121, 122, 124, 129, 131; 526/142, 150, 160, 127, 128, 143, 151, 140, 141

(56) References Cited

U.S. PATENT DOCUMENTS

| | | |
|---|---|---|
| 5,023,222 * | 6/1991 | Maezawa et al. ............... 526/153 X |
| 5,420,089 | 5/1995 | Tomotsu et al. . |
| 5,422,407 * | 6/1995 | Tomotsu et al. ................... 526/142 |
| 5,461,127 | 10/1995 | Naganuma et al. . |
| 5,527,752 | 6/1996 | Reichle et al. . |
| 5,629,391 | 5/1997 | Cardi et al. . |
| 5,830,959 * | 11/1998 | Po et al. ........................ 526/160 X |

FOREIGN PATENT DOCUMENTS

| | | |
|---|---|---|
| WO 91/13074 | 9/1991 | (WO) . |
| WO 97/21738 | 6/1997 | (WO) . |

* cited by examiner

*Primary Examiner*—Fred Teskin
(74) *Attorney, Agent, or Firm*—Oblon, Spivak, McClelland, Maier & Neustadt, P.C.

(57) ABSTRACT

A catalyst for the polymerization of vinylaromatic monomers, and particularly styrene, with a high yield and a high syndiotacticity index, comprises the product consisting of the following two components in contact with each other:

A) an $\eta^5$-cyclopentadienyl complex of titanium;

B) an organo-oxygenated compound of aluminum;

and contains a sufficient amount of at least one carboxylated product having the following general formula:

$$R\text{—}COO\text{—}G \qquad (I)$$

wherein R—COO is a carboxylic group comprising the organic radical R having from 1 to 30 carbon atoms, and G represents a hydrogen atom, an aliphatic or aromatic hydrocarbon group having from 1 to 20 carbon atoms or a metal atom, possibly substituted, linked to said carboxylic group.

23 Claims, No Drawings

CATALYST AND PROCESS FOR THE SYNDIOTACTIC POLYMERIZATION OF VINYLAROMATIC COMPOUNDS

The present invention relates to a catalyst and a process for the syndiotactic polymerization of vinylaromatic compounds.

More specifically, the present invention relates to a process for the preparation of highly syndiotactic polymers of compounds having a primary vinyl group bound to an aromatic ring, especially styrene monomers, by polymerizing these latter in the presence of a metallocene catalyst.

As is known, polymers of styrene, and particularly polystyrene, are thermoplastic materials which can be obtained with high molecular weights. Their thermal resistance, adaptability to various hot moulding techniques and excellent insulating properties, make them particularly suitable for the production of extruded, moulded or expanded articles which can be used mainly in the fields of sound and thermal insulation and as dielectric materials. Polystyrene can be obtained by the radicalic, cationic or anionic polymerization of styrene. The polymer which can be obtained radicalically, which is the one prevalently used, is an amorphous material which shows an $^1$H-NMR spectrum with wide and poorly defined bands in the chemical shift zone relating to protons of aliphatic —CH< and —CH$_2$— groups, coherent with a statistic distribution in the polymeric chain of monomeric units having a different steric configuration (atactic structure). These amorphous styrene polymers, which are transparent and relatively inexpensive, have various applications but are limited to use within a relatively limited temperature range owing to the low glass transition temperature ($T_g$) which is slightly less than 100° C. for the polystyrene homopolymer. As is known, in fact, around and above this temperature there is a softening of the polymer with a drastic deterioration in all the mechanical properties.

The normal techniques of anionic and cationic polymerization also lead to the production of a substantially amorphous polymer although, in some cases, the presence of short syndiotactic sequences of the monomeric units have been observed.

It is also known that crystalline polystyrene, prevalently isotactic, can be obtained by the stereospecific polymerization of styrene in the presence of Ziegler-Natta type catalysts, which are normally based on the combination of a halogenated compound of a transition metal with an alkyl derivative of aluminum, possibly with the addition of an electron-donor compound (Lewis base) to favour steric control.

A detailed description of the methods for obtaining isotactic polystyrene can be found, for example, in U.S. Pat. Nos. 3,161,624 and 2,882,263. This material, although potentially of great industrial interest, has never been widely distributed owing to its extremely slow and difficult crystallization, which is unacceptable in normal moulding and forming technologies.

European patent application publication number 210,615 describes a polystyrene having a structure characterized by a high degree of stereoregularity, in which the monomeric units have a regularly alternating configuration, thus producing a polymer with a syndiotactic structure. This material does not have the above disadvantages of atactic or isotactic polystyrene; it is a material which crystallizes rapidly, having a high melting point generally between 250 and 275° C., and can be oriented during transformation processes, producing end-products with excellent thermal resistance and resistance to organic solvents. These properties produce a material of great technological interest, comparable to thermoplastic technopolymers such as polyesters, polyamides, polyimides, etc.

Syndiotactic polystyrene can be prepared according to what is prepared in literature, for example, in accordance with what is described in the above European patent application, as well as in European patent application EP 272,584 and in U.S. Pat. No. 4,978,730. These preparation methods comprise the polymerization of styrene (or other styrene monomers) in bulk or in solution of an inert solvent such as toluene, at temperatures ranging from room temperature to 150° C., in the presence of a catalytic system obtained from the combination of a compound of a transition metal, normally selected from Ti, Zr, Hf, V or Ni, and an organo-oxygenated compound of aluminum, normally consisting of aluminoxane. Among the compounds of transition metals described in the art, halides, alcoholates, acetylacetonates and complexes containing at least one $\eta^5$-cyclopentadienyl ring coordinated to the metal (metallocenes), are preferably used.

Other catalytic systems suitable for the purpose are those described in published European application 421,659, consisting of compounds of boron containing fluorinated groups.

The tacticity index (syndio) specified in literature in the specific case of polystyrene, expressed as a weight percentage of polymer insoluble in methylethylketone at boiling point, is between 92 and 97% at best.

Another measure commonly used for expressing the (syndio) tacticity index is the percentage of syndiotactic dyads which can be revealed by $^{13}$C-NMR spectroscopy. The latter index may be different from the former, for instance in case of stereoblock polymers.

The mechanical, chemical and thermal properties of syndiotactic polystyrene largely depend on the percentage of stereoregularity of the polymer (syndiotacticity index). Percentages of soluble polymer of more than 2% by weight are generally sufficient to give it unsatisfactory characteristics especially in relation to resistance to organic solvents (mineral oils, oxygenated solvents) and thermal resistance. Syndiotactic polystyrenes with syndiotacticity indexes of more than 99% can normally be obtained only after extraction of the soluble part, this is an onerous process in terms of time and costs, which can preclude the use of this material for applications of high technological value.

The necessity has therefore been felt for further improvements in the field of the syndiotactic polymerization of styrene with traditional processes, aimed at increasing the stereochemical purity of the product as obtained by the polymerization process, but at the same time maintaining satisfactory yields and high molecular weights.

It is also important for the catalysts used for the preparation of syndiotactic polystyrene to be obtained with simple and rapid processes, starting from reagents which are easily available on the market.

On the other hand, it is also desirable to have production processes of syndiotactic polystyrene which enable the polymerization reaction to be carried out in relatively reduced volumes, without the necessity of using large quantities of inert liquids necessary in the traditional solution/suspension processes.

Polymerization in bulk, or with reduced quantities of diluents, could advantageously overcome this problem and it has been experimented, for example, in accordance with European patent application EP-A 584,646. It has the disadvantage however of a very slow reaction kinetics, with unsatisfactory hourly productivities and low conversions of the monomer which make it necessary to separate and recycle the non-reacted part. Furthermore, a relevant amount of atactic polymer is formed during the process, partially due to the parallel radical polymerization, especially at elevated temperature.

It would be then desirable to have catalytic systems capable of effecting bulk polymerization of styrene with a higher productivity and conversion, but at the same time maintaining a satisfactory control of the stereoregularity of the polymer obtained.

It has now been surprisingly found that using a particular catalytic system based on metallocene compounds of titanium, it is possible to polymerize styrene or other vinylaromatic compounds, either in the presence or in the absence of a liquid diluent, with high conversions of the monomer, to obtain stereoregular polymers with a high average molecular weight.

A first object of the present invention therefore relates to a catalyst for the polymerization of vinylaromatic monomers, comprising the product consisting of the following two components in contact with each other:

A) an $\eta^5$-cyclopentadienyl complex of titanium;
B) an organo-oxygenated compound of aluminum; characterized in that it contains a sufficient quantity of at least one carboxylate having the following general formula:

R—COO—G    (I)

wherein R—COO is a carboxylic group comprising the organic radical R having from 1 to 30 carbon atoms, and G represents a hydrogen atom, an aliphatic or aromatic hydrocarbon group having from 1 to 20 carbon atoms or a metal atom, possibly substituted, bound to said carboxylic group.

Another object of the present invention relates to a process for the prevalente syndiotactic polymerization of at least one vinylaromatic monomer, comprising polymerizing said at least one monomer in the presence of the above catalyst.

Other objects of the present invention will be specified hereafter.

The carboxylic group R—COO in the above carboxylate having formula (I) is of an anionic nature and can be, for example, in the form of an R—COO⁻ anionic group, wherein G is a metal cation different from Al or Ti, or in the form of an R—COO—H acid, maintaining however its anionic nature with respect to the hydrogen atom, or it can be in the form of an ester of a G hydrocarbon group, or it can be included as a ligand of an anionic nature in one or both components (A) and (B) of the catalyst, in which case G is a group containing, titanium or aluminum, respectively, bound to the carboxylic group. Particularly satisfactory results, in accordance with the present invention, have been obtained when the R—COO—G carboxylate is a compound of Al or Ti, as specified hereunder.

The organic radical R in the group R—COO, comprises from 1 to 30, preferably from 1 to 20, carbon atoms, and may additionally also contain heteroatoms such as, for example, N, O, S, X=halogen, P, Si, preferably having a very weak co-ordinating capacity, such as, for example, if the RCOO group is a carbamate group (RH donicity less than 10 Kcal/mole).

According to the above definition, preferred R radicals for the purposes of the present invention are aromatic or aliphatic, linear, cyclic or branched hydrocarbon groups, having from 1 to 17 carbon atoms. Particularly preferred among these are aliphatic, linear or branched groups, non-substituted or substituted with at least one fluorine or chlorine atom, preferably fluorine. Non-limiting examples of the above R groups are: methyl, trifluoromethyl, ethyl, propyl, isopropyl, butyl, 4-methylpentyl, neopentyl, octyl, decyl, pentadecyl, heptadecyl, 1,3,5-trimethylhexyl, cyclohexyl, phenyl, naphthyl, benzyl, 4-methylbenzyl, 4-hexylbenzyl. Other examples of R groups suitable for the purpose, in which heteroatoms are comprised, are the groups 2-furanyl, trimethylsilyl, trimethylsilylmethyl, 2-chloroethyl.

Also comprised in the present invention are catalysts containing two or more carboxylates having formula (I) mixed with each other.

The metallocene complexes which constitute component (A) in the catalyst suitable for the present invention, are preferably comprised in the following formula (II):

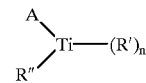

wherein:
Ti is a titanium atom in oxidation state +3 or, preferably, +4;
A is an anion containing an $\eta^5$-cyclopentadienyl ring co-ordinated to the titanium atom;
each of the R' substituents independently represents a substituent group selected from hydride, halide, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxyl group, a $C_1$–$C_{30}$ carboxylic group, a $C_2$–$C_{10}$ dialkylamide group,
R" represents a substituent group of the same nature as the previous R' groups, independently selected from these, or a second anion containing an $\eta^5$-cyclopentadienyl ring co-ordinated to the titanium, and may also be covalently bound to A by means of a divalent bridged group, so as to form a cyclic structure comprising at least 4 atoms, one of which is the titanium atom;
"n" is equal to 1 or 2 respectively when the titanium is in oxidation state +3 or +4.

According to the present invention, the group A in formula (II) is an anion containing an $\eta^5$-cyclopentadienyl ring which preferably derives (formally by extraction of a H+ ion) from a cyclopentadiene, indene or fluorene molecule, or a derivative of one of the above compounds, in which one or more carbon atoms of the molecular skeleton (comprised or not comprised in the cyclopentadienyl ring), are substituted with $C_1$–$C_8$ alkyl or silylalkyl groups, or $C_6$–$C_{10}$ aryl or aryloxy groups or $C_1$–$C_8$ alkoxyl groups. This A group may also be condensed with one or more other aromatic rings as in the case, for example, of 4,5-benzoindenyl. A groups which are particularly preferred are cyclopentadienyl ($C_5H_5$), indenyl, 4,5,6,7-tetrahydroindenyl groups and the corresponding methylsubstituted groups such as, for example, pentamethylcyclopentadienyl.

According to the present invention, the R' groups having formula (II) may, each independently, represent a hydride or halide, such as chloride or bromide, a $C_1$–$C_8$ alkyl group such as, for example, methyl, ethyl, butyl, isopropyl, isoamyl, octyl, benzyl, a $C_3$–$C_{12}$ alkylsilyl group such as, for example, trimethyl silyl, triethylsilyl, or tributylsilyl, a cycloalkyl group such as cyclopentyl or cyclohexyl, a $C_6$–$C_{10}$ aryl group such as phenyl or tolyl, a $C_1$–$C_8$ alkoxy group such as, for example, methoxy, ethyoxy, iso- or sec-butoxyl, a $C_1$–$C_{30}$, preferably $C_1$–$C_{15}$, carboxylic group or a $C_2$–$C_{10}$ dialkylamide group.

As previously specified, R" in formula (II) may represent either a group comprised in the above definition of the R' groups, or a group comprised in the above definition of A. If R' is covalently bound to the A group, it evidently represents a group comprised in the definition of R' or, respectively, A, but having a position substituted by the bond with said divalent bridge.

In a preferred embodiment of the present invention, the metallocene complex having formula (II) comprises a single $\eta^5$-cyclopentadiene group which can be identified with A, and two or three non-cyclopentadienyl groups $(R')_n$ and R", of which at least one, and preferably all, is a carboxylic R—COO group bound to the titanium so as to form a compound according to the above formula (I) in which G=substituted Ti.

In another preferred embodiment of the present invention, in which the metallocene complex having formula (II) does not comprise any group having the formula R—COO bound to Ti, the carboxylate R—COO—G having formula (I) is included in component (B).

In the above cases, it is evidently not necessary (although not excluded), in order to obtain the catalyst of the present invention, to add a carboxylate in addition to components (A) and (B), as the carboxylate is already included, in a sufficient quantity, in at least one of these components.

The metallocenes having formula (II) are generally known in the art and can be prepared with one of the usual methods suitable for the case, described in synthesis handbooks of organometallic compounds, or in the vast patent literature relating to the use of metallocenes in the polymerization of olefins. As an example, reference can be made to the publication of V. K. Gupta in "Journal of Macromolecular Science, Rev. Macromolecular Phisics, vol. C34(3) (1994) pages 439–514, as well as patent publications EP-A 416,815, EP-A 528,287, EP-A 574,794, EP-A 576,970, EP-A 577,581, WO 86/05788, U.S. Pat. No. 5,264,405 and U.S. Pat. No. 5,304,523.

Particularly for the preparation of preferred metallocene complexes in which R' and R" in formula (II) are carboxylic groups, reference can be made to the publications of P. Gomez Sal et al., "Journal of Chemical Soc., Dalton Trans." page 1575 (1991), and M. Mena et al., "Organometallics", vol. 8, page 476 (1989).

Non-limiting examples of complexes having formula (II) are listed below:
$(\eta^5$—$C_5H_5)Ti(OCOMe)_3$ $(\eta^5$—$C_5H_5)Ti(OCOPh)_2$
$(\eta^5$—$C_5H_5)Ti[OCO(CH_2)Me]_3$ $(\eta^5$—$C_5Me_5)Ti(OCOMe)_2$
$(\eta^5$—$C_5H_5)Ti(OCOPh)_3$ $(\eta^5$—Ind)Ti(OCOMe)_3$
$(\eta^5$—$C_5H_5)TiCl(OCOPh)_2$ $(\eta^5$—Ind)Ti(OCOMe)_3$
$(\eta^5$—$C_5Me_5)Ti(OCOMe)_3$ $(\eta^5$—$C_5H_5)Ti(OCOCF_3)_2$
$(\eta^5$—$C_5Me_5)Ti[OCO(CH_2)nMe]_3$ $(\eta^5$—Ind)Ti(OCOCF_3)_2$
$(\eta^5$—$C_5Me_5)Ti(OCOMe)2[OCOCH2)nMe]$
$(\eta^5$—$C_5Me_5)Ti(OCOPh)_3$ $(\eta^5$—Ind)Ti[OCO(CH_2)nMe]_3$
$(\eta^5$—$C_5Me_5)Ti(OCOBz)_3$ $(\eta^5$—$C_5H_5)Ti[OCO(CH_2)nMe]_2$
$(\eta^5$—$C_5H_5)TiCl(OCOCF_3)_2$ $(\eta^5$—$C_5Me_5)Ti[OCO(CF_2)nCF_3)_3$
$(\eta^5$—$C_5Me_5)Ti(OCOCF_3)_3$ $(\eta^5$—$C_5H_5)Ti(OCOMe)_2$
$(\eta^5$—THInd)Ti(OCOMe)_3$ $(\eta^5$—THInd)Ti(OCOCF_3)_3$
$(\eta^5$—$C_5H_5)Ti[OCOCHEt(CH_2)_3Me]_3$ $(\eta^5$—Flu)Ti[OCO(CH_2)nNMe]_3$
$(\eta^5$—$C_5Me_5)Ti[OCOCHEt(CH_2)_3Me]_3$ $(\eta^5$—Flu)Ti(OCOMe)_3$
$(\eta^5$—Flu)Ti(OCOMe)_2$ $[\eta^5$-1,3-$(CF_3)_2C_5H_3])Ti(OCOMe)_2$ In the above formulae the following abbreviations were used: Me=methyl, Ind=indenyl, THInd=4,5,6,7-tetrahydroindenyl, Flu=fluorenyl, Ph=phenyl, Bz=benzyl, Et=ethyl. The deponent "m" in the formulae in which it appears, indicates an integer between 1 and 16.

Also included in the scope of the present invention are catalysts in which the above complex having formula (II) is supported on an inert solid medium consisting, for example, of a porous inorganic solid such as, silica, alumina, silico-aluminates, possibly dehydrated and activated according to the methods known in the art, or consisting of a polymeric organic solid such as polystyrene.

The organo-oxygenated compounds of aluminum suitable as component (B) of the present invention are compounds in which at least 50% of the aluminum is bound to at least one oxygen atom and to at least one organic group consisting of a linear or branched, $C_1$–$C_{10}$ alkyl. According to the present invention, this organo-oxygenated compound of aluminum is preferably an aluminoxane. As is known, aluminoxanes are compounds containing Al—O—Al bonds, with a varying O/Al ratio, which can be obtained, according to the known technique, by the reaction, under controlled conditions, of an aluminum alkyl, or aluminum alkyl halide, with water or other compounds containing controlled quantities of water available, as, for example, in the case of the reaction of aluminum trimethyl with a salt hydrate, such as aluminum sulfate hexahydrate, copper sulfate pentahydrate and iron sulfate pentahydrate. Alurninoxanes preferably used for the formation of the polymerization catalyst of the present invention are oligo- or polymeric compounds, cyclic and/or linear, characterized by the presence of repetitive units having formula (III):

wherein $R^2$ is a $C_1$–$C_4$ alkyl group, preferably methyl.

These aluminoxanes normally contain from 4 to 70 repetitive units per molecule which may not necessarily be equal to each other, but contain different $R^2$ groups in the case of aluminoxanes with a mixed structure. Practical examples of the preparation of linear and/or cyclic aluminoxanes are provided, among others, in European patent applications EP-A-272,584 and EP-A 421,659, and in U.S. Pat. No. 4,978,730 mentioned above.

The methylaluminoxane (abbr. MAO) which is preferably used in accordance with the present invention, is a product which is commercially available both in its pure form and in the form of a solution in an inert hydrocarbon, normally toluene or heptane. Methylaluminoxane mixed with up to 10% by weight of aluminum trimethyl which improves its stability over a period of time and, indirectly, the activity as co-catalyst, is also known and commercially available.

In the catalysts for the polymerization of vinylaromatic compounds of the present invention, the two components (A) and (B) are used in such proportions that the atomic ratio between Al, in the organo-oxygenated compound, and the metal M, in the metallocene complex, is normally within the range of 50 to 5000 and preferably from 200 to 2000.

The carboxylate is conveniently present in the catalyst in a molar quantity which is at least equal to and preferably higher than the moles of metal in the metallocene. In the preferred case of metallocene-carboxylates, the ratio between carboxylic groups and metal M is equal to 3, but results in line with the high stereospecificity and activity of the catalysts of the present invention are still obtained in the case of a sufficient quantity of carboxylate either freely mixed with components (A) and (B) in the formation process of the catalyst, or contained in component (B) rather than in component (A).

According to a preferred aspect of the present invention, a catalyst for the highly syndiospecific polymerization of vinylaromatic monomers is that obtained by contact and reaction of: (A) a metallocene complex having the previous formula (II) wherein each (R')$_n$ and R" is a carboxylic group R—COO bound to Ti, wherein R is an aliphatic fluorinated or non-fluorinated group, having from 1 to 12 carbon atoms, or an aromatic group having from 6 to 15 carbon atoms, and (B) a methylaluminoxane as previously defined; in which the ratio between Al and Ti is between 50 and 2000, preferably between 100 and 1000.

Another preferred embodiment of the present invention comprises the catalyst consisting of a metallocene complex (A) of Ti not containing carboxylic groups, combined with an aluminoxane and a sufficient quantity of carboxylic groups, preferably such that the ratio RCOO/Ti is between 2 and 20. In this case the carboxylic groups can be preliminarily included in the aluminoxane, for example by adding the desired quantity of carboxylic acid to the aluminoxane, or they can be added directly to the system as third component, either in the form of carboxylic acid, or in the form of carboxylate salt of a metal preferably selected from the metals of groups 1, 2 or 13 of the periodic table of elements.

Intermediate methods and situations between those previously described are however included in the scope of the present invention (for example in the case of carboxylate partly included in the metallocene and partly included in the aluminoxane, before contact between the two components to form the catalyst).

According to the present invention, the procedure with which components (A) and (B), and the possible carboxylate, if added separately, are put in contact with each other is not critical. In particular, the preparation of the polymerization catalyst of the present invention can be carried out by addition of the components in any order. It is preferable however, when component (A) does not comprise carboxylate, for the latter to be premixed with component (B).

The above components form the catalyst of the present invention by contact and reaction with each other, preferably at temperatures ranging from room temperature to 120° C. and for times varying from 1 minute to 1 hour, more preferably from 1 to 5 minutes.

In addition, the catalyst of the present invention may also contain additives or other components normally included according to the known art, for modification or improvement, in catalysts for the stereospecific polymerization of styrene and other vinylaromatic compounds. These additives or components are, for example, inert solvents, such as aliphatic and/or aromatic hydrocarbons, weakly co-ordinating additives such as, for example, additives having a donicity DN≦10 described in Italian patent application MI95A02214, in particular pentafluoroanisole, halogenated hydrocarbons, preferably chlorinated, etc.

According to a particular aspect of the present invention, the catalyst for the syndiotactic polymerization of vinylaromatic compounds consists, in addition to components (A), (B) and the possible free carboxylate, of a further component (C) combined with the above, consisting of a compound of tin, having the following general formula (IV):

$$SnR^3R^4R^5R^6 \qquad (IV)$$

wherein the groups $R^3$, $R^4$, $R^5$ and $R^6$, the same or different, represent a linear or branched, alkyl radical preferably having from 1 to 10 carbon atoms, or an aryl orarylalkyl radical having from 6 to 14 carbon atoms.

Non-limiting examples of suitable compounds of tin having formula (IV) of the present invention are: tetramethyltin, tetraethyltin, tetra-n-propyltin, tetraisopropyltin, tetra-n-butyltin, tetraphenyltin, tetrabenzyltin, or a mixture of these.

Component (C), when comprised in the catalyst of the present invention, advantageously produces an increase in the polymerization activity, without causing any undesired effect, particularly on the stereoselectivity. It is preferably used in such a quantity that the atomic ratio Sn/Ti is between 0.001 and 100, more preferably between 1 and 50. Sn/Ti ratios lower than 0.001 do not cause any determinable variation in the properties of the catalyst with respect to this without tin; ratios higher than 100 do not provide any further advantage, but produce an undesired accumulation of tin in the polystyrene obtained at the end of the catalytic process.

The optional component (C) can be combined with the other essential components as held most suitable by the average expert. It is therefore possible, for example, to add component (C) to component (B) before adding component (A), or it is possible to add component (C) to the product formed by (A) and (B).

The catalysts of the present invention can be used with excellent results in stereospecific polymerization processes of vinylaromatic compounds to obtain syndiotactic polymers. In particular, in the presence of a diluent, in solution or suspension processes, a (syndio)tacticity index of the polymer equal to or higher than 95%, preferably equal to or higher than 98%, can be achieved. On the other hand, if used in bulk polymerization processes, in the absence of a diluent, or in the presence of a diluent in a weight ratio not higher than 1/1 with regard to the weight of the monomer, the catalyst of the present invention allows a prevalently syndiotactic polymer to be obtained, with a high molecular weight and not more than 20% by weight of the polymer being atactic.

The vinylaromatic compounds as defined in accordance with the present invention are characterized by a primary olefinically unsaturated group alpha-bound to an aromatic ring, preferably benzene. Typical polymerizable vinylaromatic compounds in the presence of the above catalyst can, for example, be represented by the following general formula (V):

$$R^7—CR^8=CH_2 \qquad (V)$$

wherein: $R^7$ represents an aryl radical, mono- or poly-cyclic, substituted or non-substituted having from 6 to 20 carbon atoms; and $R^8$ is selected from hydrogen, halogen or $C_1$–$C_4$ linear alkyl.

Non-limiting examples of compounds having formula (V) are styrene, alkylstyrenes, in which the benzene ring is substituted with one or more $C_1$–$C_4$ alkyl groups, halogenated styrenes, $C_1$–$C_4$ alkoxystyrenes, vinylnaphthalenes, such as alpha- or beta-vinylnaphthalene, vinyl-tetrahydronaphthalenes such as 1,2,3,4-tetrahydro-6-vinyl-naphthalene.

Typical examples of substituted styrenes are alpha-methylstyrene, 4-methylphenylethylene, 2-vinylnaphthalene. Styrene is particularly preferred.

A further object of the present invention therefore relates to a process for the prevalent syndiotactic polymerization of vinylaromatic compounds, which comprises polymerizing at least one vinylaromatic compound, in the presence or in the absence of a suitable inert diluent, in the presence of a sufficient quantity of a catalyst of the present invention, in accordance with what is specified above.

The above process can be carried out under the conditions normally adopted and known in the art for syndiotactic polymerization processes of styrene and other vinylaromatic monomers.

Before being fed to the polymerization zone (reactor), the vinylaromatic monomer or mixture of monomers are normally subjected to treatment to eliminate substances which can poison the catalyst, such as phenol stabilizers, water, phenylacetylene, which can consist in a distillation, passage on a molecular sieve, alumina or silica column, bulk treatment with a selective absorber solid, or a combination of these operations. The diluent, if used, is also normally subjected to this purification treatment.

The catalyst can be preformed by combination of its components, and subsequently introduced into the reactor, or each component can be introduced separately into the reactor so as to form the catalyst in situ. In the latter case, if the carboxylate is not structurally comprised in one of components (A) or (B), but forms a third component of the catalyst, it is preferable for it to be premixed with (A) or (B), more preferably (B), before being introduced into the reactor.

In effecting the polymerization process of the present invention, the diluent, if used, is preferably introduced into the reactor before or in admixture with the monomer.

The prevalently syndiotactic polymers obtained by the process of the present invention generally have high average molecular weights, normally between 100,000 and 2,000,000. The molecular weight regulation can be carried out according to one of the known techniques.

As well as for the syndiotactic polymerization of vinylaromatic monomers particularly styrene monomers, the catalysts of the present invention can also be used for the copolymerization of the same monomers with other vinyl monomers, to obtain with high yields and high productivities copolymers preferably containing up to 20% of monomeric units different from vinylaromatic units, but at the same time maintaining the same high stereoselectivity (syndio) for the latter. Monomers which are suitable for copolymerization with vinylaromatic monomers according to the present invention are, for example, primary olefins such as ethylene, propylene, 1-butene, 1-hexene.

In a preferred embodiment, the process of the present invention is carried out in solution or suspension in a suitable amount of an inert diluent. Surprisingly, under these preferred conditions, a (syndio)stereregularity of the vinylaromatic polymer equal to or higher than 95%, preferably higher than 98%, is obtained.

This allows a syndiospecific polymer with high molecular weight and excellent mechanical and thermal properties to be obtained with a high yield, without further purification or extraction phases after the polymerization step, but the separation of the diluent.

The inert diluents suitable for the purpose are, for example, aliphatic hydrocarbons liquid at the polymerization temperature, such as hexane, heptane, decane, or their mixtures, such as naphthas with a normal boiling point ranging from 80 to 150° C., or aromatic hydrocarbons such as toluene, ethylbenzene, tetrahydronaphthalene, or cycloaliphatic hydrocarbons such as cyclohexane or decaline, or mixtures of these. Preferably, the diluent is also a solvent of the polymerization catalyst.

According to this particular embodiment, the volume of diluent is preferably from 2 to 100 times the initial volume of vinylaromatic compound in the polymerization mixture. The quantity of catalyst is preferably selected so that the residence times of the polymerization mixture in the reactor are compatible with the reaction kinetics and the plant project specifications in use. Monomer/catalyst ratios are normally selected so that the molar ratio monomer/Ti is between 500 and 500,000, preferably between 1000 and 100,000. The polymerization temperature is normally selected between 0 and 120° C., preferably between 50 and 100° C. An improvement in the stereochemical (syndio) control of the reaction is normally observed in the latter temperature range.

The polymerization is preferably carried out for a time ranging from 15 minutes to 10 hours, more preferably from 30 minutes to 4 hours, depending on the temperature.

According to another preferred embodiment, the polymerization process of the present invention is carried out in the absence of a diluent (bulk polymerization), or mixed however with a limited amount of an inert liquid, at the most equal to the weight of the vinylaromatic compound itself, or, preferably, less than 30% by weight thereof This inert liquid can, for example, be the solvent used for the introduction of the catalyst, or it can have the function of facilitating some of the process operations following polymerization.

Inert liquids suitable for the purpose are essentially the same as reported before as inert diluent in general.

The quantity of catalyst is preferably selected so that the residence times of the polymerization mixture in the reactor are compatible with the reaction kinetics and the plant project specifications in use. Monomer/catalyst ratios are normally selected so that the molar ratio monomer/Ti is between 500 and 500,000, preferably between 10,000 and 500,000.

The polymerization temperature according to the preferred embodiment is normally selected between 0 and 120° C., preferably between 50 and 100° C. An improvement in the stereochemical (syndio) control of the reaction is normally observed in the latter temperature range, with respect to other metallocene compounds of titanium of the known art.

In effecting the bulk polymerization process according to the present invention, it is preferable to operate by first introducing the vinylaromatic compound into the reactor followed by the catalyst, which can be preformed by combination of its components, and subsequently introduced into the reactor, or each component can be introduced separately into the reactor so as to form the catalyst in situ. In the latter case, if the carboxylate is not structurally comprised in one of components (A) or (B), but forms a third component of the catalyst, it is preferable for it to be premixed with (A) or (B), more preferably (B), before being introduced into the reactor.

The reactor for effecting the bulk polymerization of the present invention can consist, for example, of a container, suitably equipped for feeding the reagents and catalyst and for discharging the product, which functions in batch regime, or it can consist of a continuous reactor, equipped with a system for mixing and moving the polymerization mixture appropriate for the high viscosities reached by this at high conversion degrees.

According to the process of the present invention, it is possible to carry out the bulk polymerization (possibly in the presence of limited quantities of diluent) of vinylaromatic compounds with a high polymerization kinetics and greater conversions with respect to the known catalysts not containing carboxylate groups, obtaining at the same time, a satisfactory stereochemical control of the polymerization reaction, so as to limit to less than 20% by weight, preferably less than 10%, the quantity of atactic polymer formed.

The present invention is further described by the following examples which however are purely illustrative and do not limit the overall scope of the invention itself.

The determinations by infra-red spectroscopy were carried out using an FTIR spectrometer model Perkin Elmer 1800.

The characterization by $^1$H-NMR and $^{13}$C-NMR spectroscopy mentioned in the following examples, was carried out on a nuclear magnetic resonance spectrometer mod. Bruker MSL-200.

The degree of syndiotaxy is expressed as a percentage of syndiotactic sequences in the polymer as obtained by synthesis after precipitation and drying (non-extracted polymer), measured by $^{13}$C-NMR spectroscopy.

The molecular weight measurements were carried out by gel-permeation chromatography

EXAMPLE 1

Preparation of (pentamethyl-$\eta^5$-cyclopentadienyl)-titanium Triacetate.

a) Synthesis of 1,2,3,4,5-pentamethylcyclopentane-1,3-dienyl-trimethyl-silane (Cp*SiMe$_3$)

1.43 g (36.6 mmoles) of metal potassium are added, at 0° C., to a solution of 5 g (37 mmoles) of pentamethylcyclopentadiene in 200 ml of freshly distilled tetrahydrofuran (THY). The solution is brought to room temperature and then to reflux temperature for 8 hours. A white suspension is formed to which 3.7 g (4.4 ml, 34 mmoles) of trimethylsilyl chloride, previously distilled on argon and conserved on molecular sieves are slowly added. The resulting mixture is brought to room temperature, left under stirring for 12 hours, and then filtered to give a limpid light-yellow solution. After evaporation of the solvent under moderate vacuum, 7 g of the desired product (pure Cp*SiMe$_3$) are obtained, with a yield of 77%.

$^1$H-NMR (CDCl$_3$), δ(ppm): –0.15 (s, 9H Si—Me), 1.8 (s, 15H HC—Me).

b) Synthesis of (pentamethyl-$\eta^5$-cyclopentadienyl)titanium trichloride (Cp*TiCl$_3$)

A solution of 7 g of Cp*SiMe$_3$, prepared as described above, in 50 ml of the same solvent, are added dropwise to a solution of 5 g (26 mmoles) of titanium tetrachloride (TiCl$_4$) in 200 ml of toluene. A dark red-coloured solution is formed which is maintained under stirring for ten hours at room temperature. After evaporation of the solvent under vacuum, 6.8 g of a brick-red solid are obtained which, after characterization, proves to consist of the desired compound (yield 90%).

Elemental analysis:
experimental: C, 40.8; H, 4.9;
calculated for (Cp*TiCl$_3$): C, 41.5; H, 5.3.
$^1$H-NMR (CDCl$_3$), δ(ppm): 2,3 (s, 15H $\eta^5$C—Me).

c) Synthesis of (pentamethyl-$\eta^5$-cyclopentadienyl) titaniumtrimethyl (Cp*TiMe$_3$)

A 1.6 M solution of lithium methyl in diethyl ether (ALDRICH) are slowly added to a suspension of 1 g (3.46 mmoles) of Cp*TiCl$_3$, prepared as described above, in 40 ml of n-hexane, maintained at about 0° C. in an ice-bath. The mixture is then slowly brought to room temperature, maintained under stirring for 6 hours, and finally filtered. After eliminating the solvent by evaporation under vacuum, 0.77 g of a yellow microcrystalline solid are obtained consisting of the desired compound (yield 98%). On recrystallization from pentane at –78° C., the complex is obtained in the form of yellow prisms.

Elemental analysis:
experimental: C, 68.5; H, 10.73;
calculated for (Cp*TiMe$_3$): C, 68.4; H, 10.6.
$^1$H-NMR (C$_6$D$_6$), d(ppm): 1.93 (s, 15H $\eta^5$C—Me); 0.73 (s, 9H, Ti—Me).

d) Synthesis of (pentamethyl-$\eta^5$-cyclopentadienyl)titanium triacetate Cp*Ti(OOCMe)$_3$.

1.35 ml (23.69 mmoles) of acetic acid (made anhydrous by the addition of acetic anhydride and pyridine and subsequent reflux and distillation under argon) are added dropwise to a solution of 1.8 g (7.98 mmoles) of Cp*TiMe$_3$, prepared as described above, in 150 ml of n-hexane, maintained at about 0° C. in an ice-bath. The mixture is then slowly brought to room temperature, left under stirring for three hours and slowly concentrated under vacuum. A yellow precipitate is formed, which is filtered under argon and recrystallized from a mixture of toluene/n-hexane.

2.2 g of yellow crystals are obtained, consisting of the desired compound (yield 77%).

Elemental analysis:
experimental: C, 53.5; H, 6.9;
calculated for Cp*Ti(O$_2$CMe)$_3$: C, 53.4; H, 6.7.
$^1$H-NMR (C$_6$DCl$_3$), δ(ppm): 2.01 (s, 15H $\eta^5$—C—Me); 1.78 (s, 9H, O$_2$C—Me).
IR: $v_{asymm(OCO)}$ 1540, $v_{symm(OCO)}$ 1428

EXAMPLE 2

Preparation of (pentamethyl-$\eta^5$-cyclopentadienyl)-titanium tris(trifluoroacetate)

1.82 g (15.96 mmoles) of trifluoro-acetic acid (made anhydrous by the addition of acetic anhydride and subsequent reflux and distillation under argon) dissolved in a few millilitres of n-hexane are added dropwise to a solution of 1.2 g (5.32 mmoles) of Cp*TiMe$_3$, prepared as described above, in 100 ml of n-hexane, maintained at about 0° C. in an ice-bath. The reaction mixture is then slowly brought to room temperature, left under stirring for two hours and concentrated until it becomes dry. A dark red precipitate of the desired product is formed, which is filtered under argon and washed with cold n-hexane.

Elemental analysis:
experimental: C, 37.1; H, 2.95; F,33.1
calculated for Cp*Ti(O$_2$C—CF$_3$)$_3$: C, 36.68; H, 2.87; F, 32.7
$^1$H-NMR (C$_6$DCl$_3$), δ(ppm): 1.95 (s, 15H $\eta^5$—C—Me)
IR: $v_{asymm(OCO)}$ 1759, $v_{symm(OCO)}$ 1497

EXAMPLE 3

(polymerization)

The following products are charged into a 500 ml glass reactor, equipped with a nitrogen connection, thermometer, teflon mechanical blade stirrer and feeding funnel:

200 ml of anhydrous n-heptane;
25.5 g (28.5 ml equal to 0.25 moles) of anhydrous styrene;
0.52 g (9 mmoles Al) of MAO as a 4.5M solution in toluene (WITCO).

After heating the mixture to 60° C., 52.2 mg (0.1 mmoles) of (pentamethyl-$\eta^5$-cyclopentadienyl)titanium tris (trifluoroacetate) prepared as described in example 2 are added (molar ratio styrene/Ti=2500). The polymerization is prolonged for 1 hour. At the end the polymer is separated by filtration, washed in methanol and dried in air. 2.1 g of syndiotactic polystyrene (PS) are recovered (melting p. 269.4° C.), with a productivity equal to 438 $g_{PS}/(g_{Ti}×h)$ and a yield of 40 $g_{PS}/(g_{cat}×h)$.

EXAMPLES 4 TO 8

(polymerization)

A series of polymerization tests of styrene is carried out using the same equipment and with the same catalys as the previous example 3, but modifying the conditions each time in accordance with table 1 below, which also indicates the results of the tests carried out and the characterization of the polymer obtained (syndiotactic index and melting point).

tris(isopropoxide)-($\eta^5$-cyclopentadienyl)titanium, obtained according to the method described in the above article of A. Kucht et al. on Organometallics.

TABLE 1

Syndiotactic polymerization of styrene with ($\eta^5$-pentamethylcyclopentadienyl)titanium tris(trifluoroacetate)

| Example | Sty/Ti | Al/Ti | $T_{polym.}$ (° C.) | Yield ($g_{PS}/g_{cat}$) | Productivity [$g_{PS}/(g_{Ti} \times h)$] | Melting Point (° C.) | Syndiotactic index |
|---|---|---|---|---|---|---|---|
| 3 | 2,500 | 90 | 60 | 40 | 440 | 269.4 | 98.7 |
| 4 | 5,000 | 180 | 60 | 67 | 729 | 270.1 | 98.4 |
| 5 | 5,000 | 180 | 60 | 48 | 520 | 269.2 | 97.9 |
| 6 | 5,000 | 180 | 60 | 22 | 241 | 269.8 | 97.3 |
| 7 | 5,000 | 360 | 60 | 132 | 1,440 | 270.3 | 99.0 |
| 8 | 5,000 | 720 | 210 | 182 | 601 | 271 | 98.6 |

EXAMPLE 9

(Polymerization)

A vacuum (1.4 Pa) is created in a two-necked 100 ml flask whereas the walls are heated to 100–150° C. Argon is then charged and the vacuum and filling operation is repeated. 30 ml of anhydrous toluene and 1.1 ml of a 4.5 M solution of methylaluminoxane (MAO, 5 mmoles Al) in toluene are charged under a stream of argon. After a few minutes 1 ml of an 0.025M toluene solution of the complex Cp*Ti(O$_2$C—CH$_3$)$_3$ (25 μmoles, Al/Ti ratio=200), prepared as in example 1 above, is added, by injection under argon. After aging the catalytic system for 10 minutes at 75° C., 5.8 ml (50 mmoles) of styrene are added, under argon and the mixture is left to polymerize for 2 hours (styrene/Ti ratio=2000).

At the end the polymerization is interrupted and the polymer precipitates by the addition of excess methanol. 0.9 g of polystyrene are thus obtained, which proves to be 99.2% syndiotactic (from $^{13}$C-NMR characterization) with a melting point of 270.1° C. (from scan differential calorimetry, DSC). The overall yield is 375 $g_{PS}/(g_{Ti}\times h)$.

EXAMPLES 10 To 12

(polymerization)

Three further polymerization tests of styrene are carried out using the same procedure and catalyst as example 9 above, but modifying the conditions each time in accordance with table 2 below, which also indicates the results of the tests carried out.

At the end a productivity of 285 $g_{PS}/(g_{Ti}\times h)$ was obtained. The polystyrene thus prepared had a syndiotactic index of 94.5 and a melting point of 253° C.

EXAMPLE 14

(I) Preparation of MAO containing acetate 10 ml of a 4.5M toluene solution of MAO are charged into a 2-necked 50 ml flask, placed under argon according to the procedure described above. 0.34 ml of a 1M solution of acetic acid in toluene (0.34 mmoles, Al/(acetate)=133) are then added and the mixture is left to age under slow stirring for 10 minutes at room temperature, before use.

(II) Polymerization 30 ml of anhydrous toluene and 2.3 ml of the MAO solution and acetate prepared as above (10 mmoles Al, 75 mmoles acetate) are charged into a two-necked 100 ml flaskm prepared as described in the previous example 9, under a stream of argon. After a few minutes 1 ml of an 0.025M toluene solution of the complex Cp*TiMe$_3$ (25 μmoles, Al/Ti ratio=400), prepared as in example 1 above, is added, by injection under argon. After aging the catalytic system for 10 minutes at 65° C., 5.8 ml (50 mmoles) of styrene are added, under argon and the mixture is left to polymerize for 2 hours (styrene/Ti ratio=2000).

TABLE 2 syndiotactic polymerization of styrene with ($\eta^5$-pentamethylcyclopentadienyl)titanium triacetate

| Example | Al/Ti | $T_{polym.}$ (° C.) | Yield ($g_{PS}/g_{cat}$) | Productivity [$g_{PS}/(g_{Ti} \times h)$] | Melting Point (° C.) | Syndiotactic index |
|---|---|---|---|---|---|---|
| 9 | 200 | 75 | 101 | 375 | 270.1 | 99.2 |
| 10 | 300 | 75 | 56 | 208 | 270.6 | 99.1 |
| 11(*) | 200 | 75 | 84 | 625 | 270.3 | 99.2 |
| 12 | 200 | 25 | 40 | 146 | 268.4 | 97.6 |

(*)50 μmoles of Ti, with the same molar ratios with respect the other species and styrene.

EXAMPLE 13

(comparative)

A polymerization test of styrene is carried out using the same equipment and under the same conditions as the previous example 9, with Al/Ti=200 and Sty/Ti=2000, but using, as catalytic component, the complex of the known art At the end the polymerization is interrupted and the polymer precipitates by the addition of excess methanol. 0.8 g of polystyrene are thus obtained, which proves to be 99.1% syndiotactic (from $^{13}$C-NMR characterization) with a melting point of 269.7° C. (from scanning differential calorimetry, DSC). The overall yield is 334 $g_{PS}/(g_{Ti}\times h)$.

EXAMPLE 15

(comparative)

A polymerization test of styrene is carried out using the same equipment and under the same conditions as the previous example 14, with Al/Ti=400 and Sty/Ti=2000, but using as catalyst, the complex Cp*TiMe$_3$ combined with MAO not treated with acetic acid.

At the end 0.23 g of polystyrene were obtained having a syndiotactic index of 96.2 and a melting point of 268.5.

EXAMPLE 16

(bulk polymerization)

The following components are charged, in order, into a 50 ml glass tailed test-tube, at room temperature and in a stream of nitrogen:

- 10 ml (equal to 0.087 moles) of anhydrous styrene purified by passage on a basic alumina column;
- 0.33 ml (0.522 mmoles Al) of a solution of MAO 1.57 M in toluene (WITCO) (molar ratio Al/Ti=600);
- 0.28 ml of a solution 3.14×10$^{-3}$ M in toluene of (pentamethyl-η$^5$-cyclopentadienyl)titanium tris

EXAMPLE 23

(comparative)

A syndiotactic polymerization test of styrene is carried out basically under the same conditions and with the same reagents as the previous example 22 (see table 3), with the only difference that the titanium complex used is (pentamethyl-η$^5$-cyclopentadienyl)titanium triphenoxide [Cp*Ti(OPh)$_3$].

As can be seen in table 3 below, the conversion of styrene into syndiotactic polymer is much less than that obtained, under the same conditions, with the catalysts based on the carboxylic complexes of titanium of the present invention.

TABLE 3

Mass polymerization of styrene with (pentamethyl-η$^5$-cyclopentadienyl)titanium tris(trifluoroacetate)

| Example | Styrene (g) | Catalyst Type | Ti (moles × 10$^6$) | Sty/Ti (mol/mol) | Al/Ti (mol/mol) | T$_{polym.}$ (° C.) | PS$_{tot.}$ (g) | Ins. Fract. (sPS/PS %) | Productivity (Kg$_{sPS}$/g$_{Ti}$) | Molecular weight |
|---|---|---|---|---|---|---|---|---|---|---|
| 16 | 9.06 | Cp*Ti(O$_2$C—CF$_3$)$_3$ | 0.83 | 100,000 | 600 | 60 | 2.5 | 79.6 | 47.6 | 1,582,000 |
| 17 | 18.02 | Cp*Ti(O$_2$C—CF$_3$)$_3$ | 1.70 | 103,000 | 618 | 90 | 11.2 | 91.0 | 125 | 424,000 |
| 18 | 18.02 | Cp*Ti(O$_2$C—CF$_3$)$_3$ | 0.85 | 206,000 | 1238 | 90 | 4.1 | 83.8 | 84.5 | 807,000 |
| 19 | 19.09 | Cp*Ti(O$_2$C—CF$_3$)$_3$ | 0.63 | 304,000 | 1525 | 90 | 5.14 | 84.6 | 144 | 781,000 |
| 20 | 18.02 | Cp*Ti(O$_2$CMe)$_3$ | 1.69 | 103,000 | 615 | 90 | 9.94 | 91.8 | 113 | 454,000 |
| 21 | 18.02 | Cp*Ti(O$_2$CMe)$_3$ | 0.85 | 206,000 | 1230 | 90 | 6.3 | 90.1 | 140 | 449,000 |
| 22 | 9.06 | Cp*Ti(O$_2$C—CF$_3$)$_3$ | 3.12 | 28,000 | 300 | 90 | 5.25 | 85.8 | 30.1 | 416,000 |
| 23* | 17.05 | Cp*Ti(OPh)$_3$ | 6.00 | 28,000 | 300 | 90 | 5.3 | 83.5 | 15.4 | 408,000 |

*Comparative example (trifluoroacetate) (8.70×10$^{-7}$ moles) prepared as in example 2 (molar ratio styrene/Ti=100,000).

The mixture is briefly stirred and the temperature is then brought to 60° C. The polymerization of the styrene is activated and is prolonged for 2 hours. At the end the mixture is suspended in 200 ml of methanol acidified with 0.5 ml of concentrated HCL. After filtration, washing with methanol and drying, 2.5 g of polymer are recovered, the $^1$H-NMR of which shows the presence of a minor amount of atactic polystyrene. The polymer is then extracted with methylethylketone at reflux temperature for 8 hours. The remaining insoluble fraction proved to consist of 2.0 g of substantially syndiotactic polystyrene (79.5% by weight with respect to the total amount of polymer obtained; stereoregularity greater than 99.9%), as can be seen from the measurement of the percentage of syndio dyads by $^{13}$C-NMR spectroscopy. No mixed stereoblock (syndio +atactic) polymer was formed.

The conversion to syndiotactic PS was 21.8% with respect to the initial styrene, with a productivity equal to 47.6 Kg$_{sPS}$/g$_{Ti}$.

EXAMPLES 17–22

(bulk polymerization)

A series of polymerization tests of styrene is carried out using the same procedure as the previous example 16, but modifying each time, the conditions, the catalyst and the relative quantities of reagents in accordance with table 3 below, which also indicates the results of the tests carried out and the characterization of the polymer obtained (molecular weight, insoluble fraction).

EXAMPLE 24

The following components are charged, in order, into a 50 ml glass tailed test-tube, at room temperature and in a stream of nitrogen:

- 20 ml (equal to 0.175 moles) of anhydrous styrene purified by passage on a basic alumina column;
- 0.66 ml of a solution of MAO 1.57 M in toluene (1.05 mmoles Al; molar ratio Al/Ti=1238);
- 0.44 ml of a solution of tin tetraphenyl 0.001 M in toluene (4.4×10$^{-6}$ moles of Sn, ratio Sn/Ti=5.2);
- 0.27 ml of a solution 3.14×10$^{-3}$ M in toluene of (pentamethyl-η$^5$-cyclopentadienyl)titanium tris (trifluoroacetate) (8.48×10$^{-7}$ moles) prepared as in example 2 (molar ratio Sty/Ti=206,000).

The mixture is briefly stirred and the temperature is then brought to 90° C. The polymerization of the styrene is activated and is prolonged for 2 hours. At the end the mixture is suspended in 200 ml of methanol acidified with 0.5 mnl of concentrated HCL. After filtration, washing with methanol and drying, 8.26 g of polymer are recovered which, after extraction according to what is specified above in example 16, gave 7.46 g of substantially syndiotactic polystyrene (insoluble fraction 90.4% by weight, syndio stereoregularity >99.9%). The conversion to syndiotactic PS was 41% with respect to the initial styrene, with a productivity equal to 184 Kg$_{sPS}$/g$_{Ti}$.

EXAMPLE 25

A polymerization test was carried out with the same procedure and the same reagents as example 24 above, but using the following molar ratios between the reagents: Sty/Ti=304,000; Al/Ti=1525; Sn/Ti=5.2.

At the end, 5.83 g of polystyrene were obtained which, after extraction (insoluble fraction 88.9%) gave syndiotactic polystyrene with a productivity equal to 157 kg$_{sPS}$/g$_{Ti}$.

What is claimed is:

1. A catalyst for the polymerization of vinylaromatic monomers, comprising the product obtained by contacting with each other the following two components (A) and (B):

(A) an $\eta^5$-cyclopentadienyl complex of titanium;

(B) an organo-oxygenated compound of aluminum;

wherein said catalyst contains at least one carboxylate having the following formula:

  (I)

wherein R—COO is a carboxylic group comprising the organic radical R having from 1 to 30 carbon atoms, and G independently represents hydrogen or a metal atom, wherein said $\eta^5$-cyclopentadienyl titanium complex has the following formula (II):

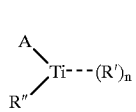  (II)

wherein:

Ti is a titanium atom in oxidation state +3 or +4;

A is an anion containing an $\eta^5$-cyclopentadienyl ring co-ordinated to the titanium atom;

each of the R' substituents and R" independently represents a substituent group selected from hydride, halide, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxy group, a $C_1$–$C_{30}$ carboxylic group, and a $C_2$–$C_{10}$ dialkylamide group;

or R" represents a second anion containing an $\eta^5$-cyclopentadienyl ring co-ordinated to the titanium, and may also be covalently bound to A by means of a divalent bridged group, so as to form a cyclic structure comprising at least 4 atoms, one of which is the titanium atom, "n" is equal to 1 or 2 respectively when the titanium is in oxidation state +3 or +4.

2. The catalyst according to claim 1, wherein said organic radical R is selected from linear, cyclic or branched, aliphatic hydrocarbons, having from 1 to 17 carbon atoms, optionally substituted with at least one fluorine atom.

3. The catalyst according to claim 1, wherein the group A is selected from cyclopentadienyl ($C_5H_5$), indenyl, 4,5,6,7-tetrahydroindenyl groups and the corresponding methyl substituted groups, and the group R" is a substituent group.

4. The catalyst according to claim 1, wherein at least one of the groups R' and R" is a carboxylic group bound to the titanium.

5. The catalyst according to claim 4, consisting essentially of said product wherein all the groups R' and R" are R—COO carboxylic groups bound to the titanium.

6. The catalyst according to claim 1, which comprises the product obtained by contact and reaction of:

(A) said complex, wherein each (R')n and R" is a carboxylic group R—COO bound to Ti, wherein R is an aliphatic fluorinated or non-fluorinated group, having from 1 to 12 carbon atoms, or an aromatic group having from 6 to 15 carbon atoms, and (B) a methylaluminoxane;

wherein the ratio of Al to Ti is between 50 and 2000.

7. The catalyst according to claim 1, wherein component (B) comprises the carboxylate R—COO—G having formula (I).

8. The catalyst according to claim 7, wherein component (B) is obtained, before contact with component (A), by adding said carboxylate to an aluminoxane, in such a quantity that the ratio RCOO/Ti is between 2 and 20.

9. The catalyst according to claim 1, also comprising a component (C) combined with components (A) and (B), wherein component (C) is a compound of tin, having the following formula (IV):

$$SnR^3R^4R^5R^6$$  (IV)

wherein the groups $R^3$, $R^4$, $R^5$ and $R^6$, the same or different, represent a linear or branched, alkyl radical, or an aryl or arylalkyl radical having from 6 to 14 carbon atoms.

10. The catalyst according to claim 9, wherein said compound of tin having formula (IV) is used in such a quantity that the atomic ratio Sn/Ti is between 1 and 50.

11. A process for the preparation of a prevalently syndiotactic polymer of at least one vinylaromatic compound, comprising polymerizing said compound at temperatures ranging from 0 to 120° C., in the presence of the catalyst according to claim 1.

12. The process according to claim 11, wherein said vinylaromatic compound is styrene.

13. The process according to claim 11, which is carried out in solution or suspension of an inert diluent, in a quantity ranging from 2 to 100 times the volume of said vinylaromatic compound in the polymerization mixture.

14. The process according to claim 13, wherein the inert diluent is an aliphatic or aromatic hydrocarbon, liquid at the polymerization temperature.

15. The process according to claim 11, wherein the molar ratio between the vinylaromatic compound and the titanium in the catalyst is between 1,000 and 100,000.

16. The process according to claim 11, wherein the polymerization temperature is between 50 and 100° C.

17. The process according to claim 11, which is carried out in the absence of a diluent, or in the presence of a limited amount of an inert liquid, at the most equal to the weight of the vinylaromatic compound itself.

18. The process according to claim 17, wherein said inert liquid is present in an amount less than 30% by weight with respect to the vinylaromatic monomer.

19. The process according to claim 17, wherein the molar ratio of said vinylaromatic compound to the titanium in said catalyst is between 10,000 and 500,000.

20. The process according to claim 17, wherein the temperature is between 50 and 100° C.

21. The catalyst according to claim 6, wherein the ratio of Al to Ti is between 100 and 1000.

22. The catalyst according to claim 8, wherein said carboxylate is carboxylic acid.

23. The catalyst according to claim 9, wherein the alkyl radical has 1 to 10 carbon atoms.

* * * * *